United States Patent [19]

Meshberg

[11] Patent Number: 5,433,343
[45] Date of Patent: Jul. 18, 1995

[54] DELIVERY SYSTEM FOR MEASURED QUANTITIES OF LIQUIDS, ESPECIALLY MEDICATIONS

[76] Inventor: Philip Meshberg, 2770 S. Ocean Blvd., Apartment 602, Palm Beach, Fla. 33480

[21] Appl. No.: 111,330

[22] Filed: Aug. 24, 1993

Related U.S. Application Data

[63] Continuation-in-part of Ser. No. 99,386, Jul. 30, 1993.

[51] Int. Cl.⁶ ............................................. B67D 5/00
[52] U.S. Cl. ................................. 222/25; 222/43; 222/82; 222/154; 222/162; 222/183; 222/309; 222/323; 222/562; 239/390
[58] Field of Search ................. 222/23, 43, 154, 162, 222/158, 309, 321, 182, 183, 190, 25, 29, 282, 283, 288, 386, 562, 82, 83, 323; 239/390, 391, 600

[56] References Cited

U.S. PATENT DOCUMENTS

| | | | |
|---|---|---|---|
| 2,914,222 | 11/1959 | Meshberg | 222/162 |
| 2,966,283 | 12/1960 | Darvie | 222/162 X |
| 3,141,583 | 7/1964 | Mapel et al. | 222/82 X |
| 3,211,346 | 10/1965 | Meshberg | 222/263 |
| 3,254,803 | 6/1966 | Meshberg | 222/182 |
| 3,779,462 | 12/1973 | Bruninga | 239/390 X |
| 4,131,217 | 12/1978 | Sandegren | 222/82 |
| 4,175,704 | 11/1979 | Cohen | 222/320 X |
| 4,185,755 | 1/1980 | Sachs et al. | 222/309 X |
| 4,445,626 | 5/1984 | Steffen et al. | 222/309 X |
| 4,454,964 | 6/1984 | Sacher | 222/309 X |
| 4,463,880 | 8/1984 | Krammer et al. | 222/189 |
| 4,771,769 | 9/1988 | Hegemann et al. | 222/162 X |
| 4,871,092 | 10/1989 | Maerte | 222/309 X |
| 4,946,069 | 8/1990 | Fuchs | 222/43 |
| 5,024,355 | 6/1991 | Jouillat et al. | 222/162 |
| 5,152,435 | 10/1992 | Stand et al. | 222/321 |
| 5,226,563 | 7/1993 | Coggiola | 222/162 X |
| 5,244,122 | 9/1993 | Botts | 222/158 X |
| 5,273,189 | 12/1993 | Jouillat et al | 222/321 X |
| 5,328,055 | 7/1994 | Battle | 222/105 X |

FOREIGN PATENT DOCUMENTS

| | | |
|---|---|---|
| 0070385 | 1/1983 | European Pat. Off. . |
| 0098939 | 1/1984 | European Pat. Off. . |
| 0452728 | 10/1991 | European Pat. Off. . |
| 0509863 | 10/1992 | European Pat. Off. . |
| 2658486 | 8/1991 | France . |
| WO91/13689 | 9/1991 | WIPO . |
| WO92/00812 | 1/1992 | WIPO . |

*Primary Examiner*—Kevin P. Shaver
*Attorney, Agent, or Firm*—Kenyon & Kenyon

[57] ABSTRACT

The present invention relates to a dispenser for dispensing medications into the nostril or intravenously. The device has a number of advantageous features. First, the device includes a pump in the outer package, so that it may be used with conventional medication packaging. Second, it includes a stop mechanism for allowing adjustment of the dose to be dispensed. Finally, the device is adapted to be used for both nasal and intravenous dispensing, via a replaceable spray passage or injection needle. The device can also have indicia for indicating when the last dose was dispensed, and can include a disinfecting feature for the spray head. The device can also have a gripping feature which spaces the fingers from the nostril into which medication is dispensed. The package is preferably clear so that the user can determine the quality of the medication being dispensed. The device is particularly useful for dispensing medications such as insulin.

38 Claims, 2 Drawing Sheets

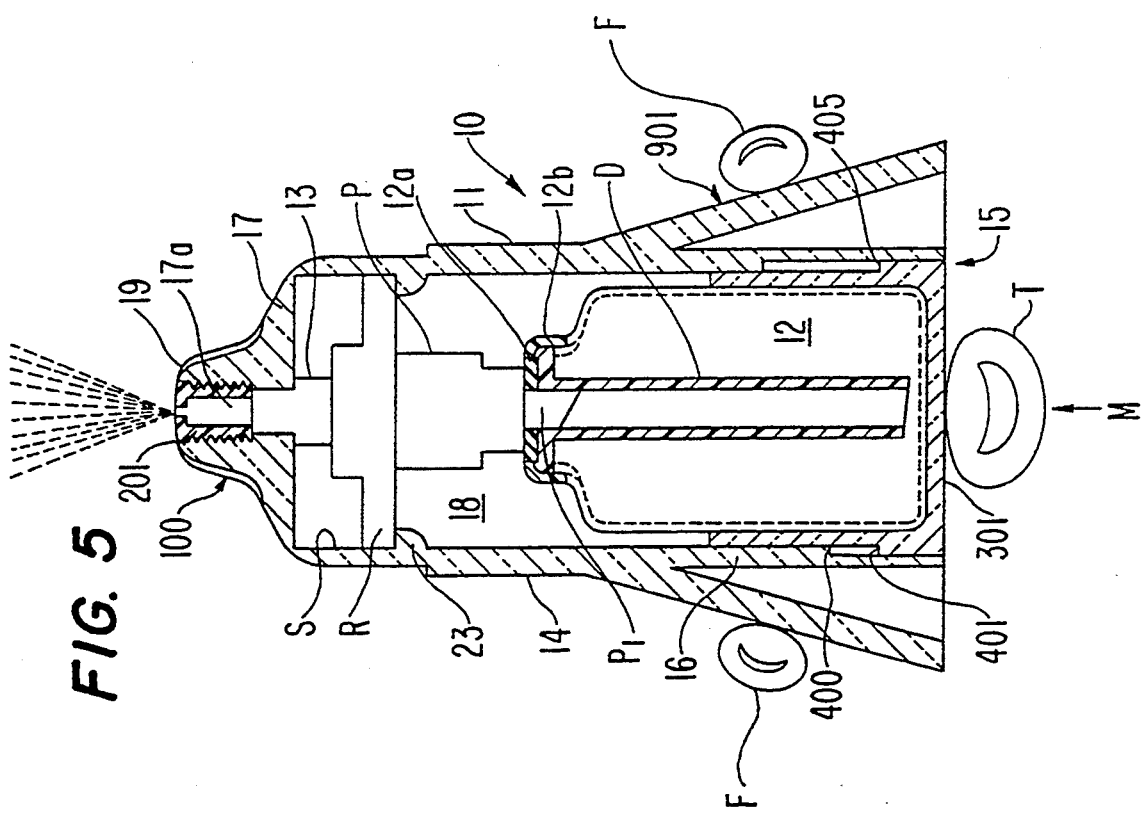
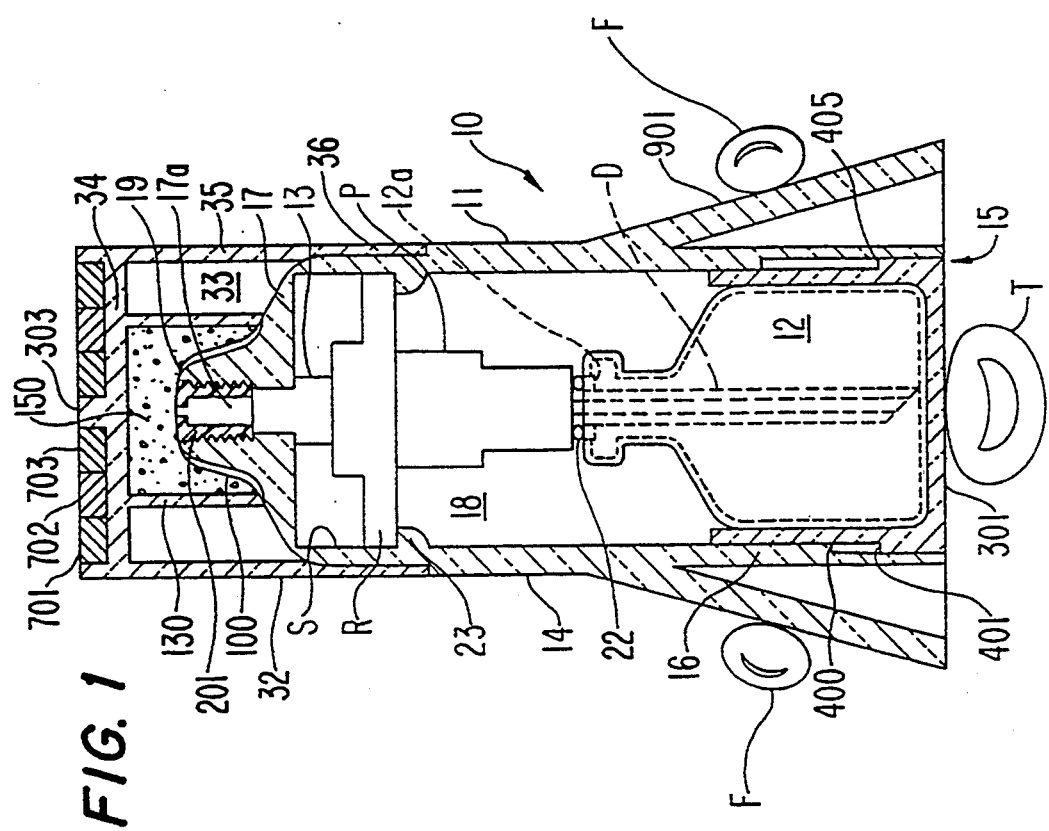

DELIVERY SYSTEM FOR MEASURED QUANTITIES OF LIQUIDS, ESPECIALLY MEDICATIONS

RELATED APPLICATIONS

This application is a continuation-in-part of U.S. patent application Ser. No. 08/099,386 filed Jul. 30, 1993.

BACKGROUND OF THE INVENTION

1. Field of the Invention

This invention relates to a device for dispensing measured quantities of liquids. The device is particularly useful for dispensing medications in accurate metered quantities, either nasally or intravenously. The invention allows an end user to adjust the quantity of material dispensed in each metered dose. The invention includes a container for the material to be dispensed and a relatively movable operating device projecting outwardly of the container for dispensing the material via a pump mounted on the operating device. Because the dispensing pump is mounted on the operating device, the invention can be used with conventional containers used to hold medications for intravenous injection. One type of medication which the present invention is particularly useful for dispensing is insulin, which may be administered in accurate metered doses either nasally or intravenously with the device of the present invention. Furthermore, because the pump is not mounted in the container, it may be reused - - - requiring less waste than a conventional container with a pump which is thrown away with the container when the container is emptied.

2. Description of the Related Art

U.S. Pat. No. 3,254,803 shows a device for dispensing quantities of liquid in the form of a spray into a nasal cavity. The device of this patent uses an aerosol container mounted in a dispensing package for dispensing a metered quantity of liquid. The device of U.S. Pat. No. 3,254,803 does not, however, allow a user to select or vary the quantity of liquid delivered with each dose, since the amount delivered is dependant upon the structure of the metering valve within the aerosol container. This device also is not intended to be used with a conventional medication container, and is not adapted to allow intravenous injection.

U.S. Pat. No. 3,211,346 shows a device for dispensing liquid under the action of a pump, in which the pump is mounted to a non-vented container pressurized by a quantity of inert gas. This type of device, in which the material to be dispensed does not come into contact with air until it exits the spray head, is particularly useful for dispensing medications, which could degrade if placed in contact with the air used to vent a conventional piston-operated dispensing pump. The device of U.S. Pat. No. 3,211,346 does not contain any mechanism for limiting the length of the stroke of the pump. The only metered quantity that this pump can dispense is that quantity that comes when the pump is depressed through its full stroke. Furthermore, in this device the pump is mounted in the container, with the result that the pump is disposed of when the container is empty.

U.S. Pat. No. 5,363,992 and U.S. patent application Ser. No. 08/012,196 show mechanisms for limiting the length of stroke of a spray pump, to thereby allow the pump to dispense a number of different metered quantities of liquid material. The devices of these patent applications are designed to be used with spray pump devices which use a finger-operated reciprocating actuator, and include mechanisms whereby a conventionally-styled actuator interacts with a stroke limiting device to control the amount of liquid dispensed. These devices also include different spray nozzles for different particle sizes, with differently structured break-up devices. The devices of these patent applications are not suited for a spray nozzle which is inserted nasally, since such devices do not use a conventionally-styled actuator.

U.S. patent application Ser. No. 08/099,386, the substance of which is incorporated here in by reference, shows a device for dispensing liquids, particularly medications, nasally. This device shows a mechanism for limiting the stroke of the pump, to ensure accurate and adjustable quantities of the liquid dispensed. This device, however, uses a liquid container which includes a pump, and is therefore not useable with conventional containers for liquid medical products. Furthermore, this device can only be used to dispense liquids nasally, and cannot dispense liquids intravenously as well.

SUMMARY OF THE INVENTION

It is an object of the invention to provide a package for a material dispensing device which facilitates the relative movement of a container for the material being dispensed and an operating member projecting from the container through which the material is dispensed.

It is also an object of the invention to provide a material dispensing device including a housing open at one end and providing a cavity for removably receiving a container, the housing being provided with a pump engageable with the container for dispensing material from the container, especially a container in which medications are conventionally stored for intravenous use. The container is engageable through the open end of the housing or via a driving piston for imparting a force thereto for moving it in the housing relative to the operating member. The housing can have opposed outwardly flared walls formed integral with and of substantially the same thickness as the side walls, against which force may be applied in a direction opposed to the force applied to the container for relatively moving the container and operating member to dispense the material. The housing can be constructed of a transparent material, so that easy visual inspection can be made of the dispensed medication, to insure that it has not deteriorated.

Another object of the invention is to provide a package for a material dispensing device including a container receiving housing and a removable cover member therefor. The cover member may have a disinfectant mechanism which contacts the spray nozzle every time the cover is placed on the housing, thereby preventing bacteria or other undesirable microorganisms from developing or growing on the spray nozzle.

Yet another object of the invention is to provide a package for a material dispensing device that facilitates the relative movement of the material container and operating member so that the material is dispensed. The package includes a replaceable mechanical breakup device for the material being dispensed, the breakup device being positioned adjacent and within the applicating nozzle. The invention also includes a replaceable needle which can be used to dispense material intravenously.

It is further an object of the invention to provide a package for a device for dispensing materials using a reciprocating pump. The container and pump should be non-vented, to prevent the contact of air with the product to be dispensed within the container. By using a non-vented pump, the product to be dispensed is prevented from being degraded by contact with air in the container. The use of a pump allows the adjustment, through suitable stop mechanisms, to control the length of stroke of the pump, and thereby the amount of the dose dispensed with each actuation of the pump. The package includes a pump connectable with the container through which material is dispensed. The package includes a housing open at one end and having a side wall portion of substantially uniform thickness and a closed end portion. The container is adapted to be removably received in the housing. The pump is mounted in the housing and includes a dip tube or tail piece intended to pierce the seal of a medication container. The pump also includes a seal for sealing the container to the pump. The container is engageable through the open end of the housing by finger pressure on a driving piston mechanism for applying a force thereto for moving the container relative to the pump stem. The side wall portion of the housing is formed with opposed integral flared walls projecting outwardly from the housing, or with stepped portions projecting outwardly therefrom, of substantially the same thickness as the side wall portions. These projecting portions are used to provide an opposing force to the finger force used to actuate the pump.

It is still further an object of the invention to provide a package for material dispensing which is adapted to be manufactured by quantity production methods, is readily assembled, and is of such rugged character it will function over long periods of time with freedom from all difficulties.

It is another object of the invention to provide a nasal dispenser which allows the drawing in of air through the nose during dispensing to assist in the inhalation of medication. It is another object of the invention to provide a dispenser with indicia for indicating the size, time and date of the last dispensed dose. It is another object of the present invention to provide a dispenser which allows the fingers to be kept away from the nostril during dispensing, and which allows the easy disinfecting of the spray nozzle between use. It is finally an object of the present invention that is adaptable for dispensing both nasally and intravenously.

DESCRIPTION OF THE DRAWINGS

Other objects and advantages of the invention will be apparent from he specification and claims, when considered in connection with the attached sheets of drawings, illustrating one form of the invention, wherein like characters represent like parts and in which:

FIG. 1 is an elevational view, in section, of a first embodiment of the present invention;

FIG. 5 is an elevational view in section of a second embodiment of the present invention.

DETAILED DESCRIPTION OF THE INVENTION

Figure 2:
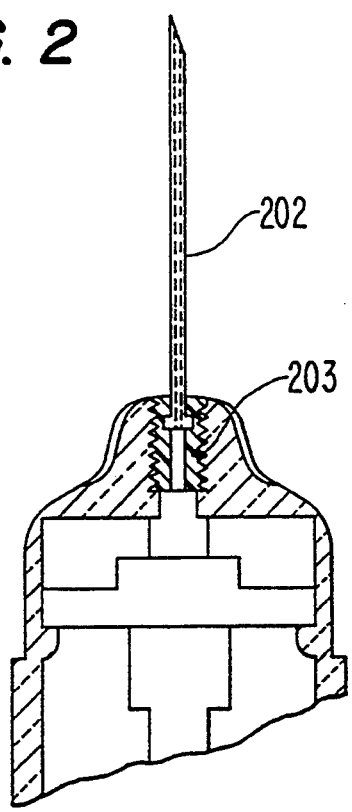
FIG. 2 is a partial view, showing an adaptation for intravenous use for the embodiment of FIG. 1.
Figure 3:
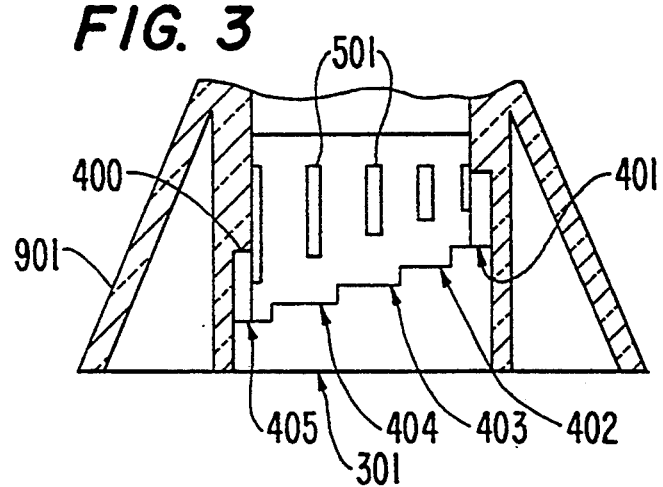
FIG. 3 is a partial view, in partial section, of the stroke limiting device of the present invention.
Figure 4:
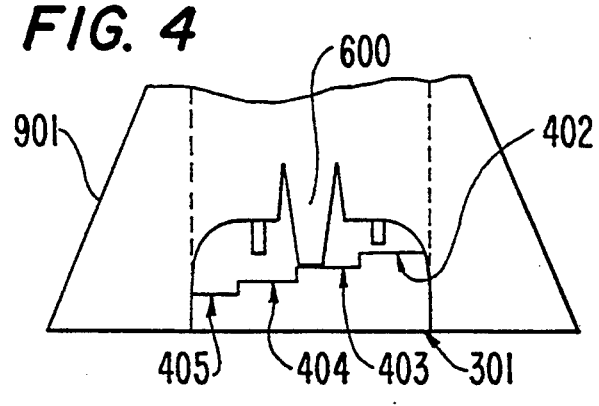
FIG. 4 is a partial view of the rotational-locking device of the present invention.

Referring now to the drawings for a more detailed description of the invention, FIGS. 1-4 show a first embodiment of the material dispensing device 10 of the present invention.

While the packaging concepts of the present invention are applicable to a variety of dispensing devices, which include a container for the material to be dispensed and a dispensing operating member connected thereto, in the herein illustrated form of the invention the device 10 comprises a well known material dispensing pump P (i.e., like the pump shown in U.S. Pat. No. 3,211,346, the substance of which is incorporated herein by reference) and container 12 of the type used to hold medications for intravenous use. The pump P has a reciprocable operating member or pump stem 13 projecting outwardly of the pump P for operating the pump on being moved relative thereto. The operating member is formed with an axial passage (not shown) through which the material is dispensed. The container 12 is preferably filled with a medication which may enter the blood stream when dispensed into the nasal cavity or intravenously, for example, a medication like insulin.

It is common practice in the material dispensing art, and particularly in the field of spray pump devices, to package the dispensing device for decorative or protective reasons. In most material dispensing devices, spraying is initiated by displacement of an actuator by finger pressure. In certain devices, however, such a nasal applicators, or the like, an actuator may not be used, since the spray nozzle is inserted in the nasal passage. In such a device, another mechanism must be provided for operating the device.

The dispensing package 11, according to the present invention, in addition to forming the conventional decorative and protective casing for the device 10, provides the mechanism for relatively moving the material container 12 and its dispensing pump stem 13 to operate the device. In the device of the present invention, the pump stem 13 is fixedly mounted in the closed end 17 of the housing 14. Operation of the pump P is by upward movement of the pump P relative to the stem 13. When the container 12 is pushed upwardly, the top of the container 12 pushes the pump P upwardly, so that the outer rim R slides against a surface S in the cavity 18. The upward movement of the pump P relative to the pump stem 13 acts to pressurize and dispense material in the pump P. A retaining ridge 23 limits downward movement of the pump P in the package 11.

The pump P includes a dip tube D for insertion into container 12. Dip tube D includes a end portion E which is pointed and which pierces a seal 12a at the top of the container 12. The bottom portion of the pump P includes a seal 22, which can, e.g., be in the form of an O-ring mounted in the bottom of the pump P for sealing the interior of the container 12 from the atmosphere after the seal 12a has been pierced.

As illustrated, the package 11, which may be molded or similarly formed from plastic or like material and may be inserted into a nasal passage, includes a housing 14, open at one end as at 15, having a cylindrical side wall portion 16 of the substantially uniform thickness and closed end portion 17. The package 11 is preferably molded of a transparent plastic material, so that easy visual inspection of the contents of container 12 can be made. This allows the end user to tell if the medication to be dispensed is clear or cloudy, and therefore whether it is of a proper quality for safe use.

The side wall portion 16 and closed end portion 17 define within the housing a cavity 18 that holds the container 12 and is adapted to movably receive the container therein. As clearly shown in FIG. 1, the container is engageable through the opposite end 15 of the housing for applying a force thereto, as by thumb T pressure or the like, for moving the container in the cavity. The thumb T pressure could be applied directly to the container 12, or as shown in FIG. 1, could be applied to a driving piston 301 slidable in the open end 15 of the housing.

The closed end portion 17 of the housing 14 is formed with recess 17a which provides communication between the pump P and the exterior of the housing. The recess is adapted to receive and frictionally retain the operating member 13 of the pump P so that the passage communicates with the exterior of the housing and the pump stem 13 is held in position relative to the package 11. While the closed end portion 17 of the housing and the recess 17a therein may take many forms, depending upon the ultimate use of the device 10, in the herein illustrated form of the invention the closed end portion is formed with a boss 19, providing a nozzle or applicator tip for insertion into a nasal passage, and the recess includes a passage extending through the boss 19. The boss 19 is shaped so as to limit the amount of penetration of the boss 19 into the nasal passage. The boss 19 may advantageously include one or more air grooves 100 channeled in the surface of the boss 19. The air grooves 100 allow the user to draw in air through the nose as material is being dispensed from the package 10, thereby assisting in the delivery of the medication in container 12 to the bloodstream of the individual user.

The dispensing device may include a replaceable dispensing passage 201 which can be inserted and replaced in the boss 19, and may include a conventional mechanical breakup device (not shown). The replaceable dispensing passage 201 can be held in the boss 19 by means of, e.g., screw threads. When it is desired to use the dispensing device for intravenous injection, a replaceable needle 202 may be inserted in the boss 19 via a retaining element 203 with, e.g., screw threads.

In order to dispense the material from the container 12, by relatively moving the container and the housing carrying the dispensing operating member 13, shoulders 901 are provided on opposite sides of the housing against which a force, such as finger F pressure, may be applied in a direction opposed to the force moving the container through the open end 15 of the housing. While the shoulders 901 may be provided in any known manner and take any desired form, in one form of the invention illustrated they comprise outwardly flared wall portions. It will be noted that the outwardly flared wall portions which have their sides gently tapering into the surface of the housing side wall portion 16, are of substantially the same thickness as the side wall portion to eliminate strains and the like when the dispensing package is manufactured by a molding operation or the like.

In order to complete the dispensing package 11 and protect the boss 19 when the applicator is not in use, a removable cover member 32 is provided as shown in FIG. 1. The cover member, which may be formed of the same material and in a manner similar to the package housing 14 and defines a chamber 33 for receiving the closed end portion of the housing, has an end wall 34 and a side wall portion 35, the latter including a depending annular skirt 36 for frictionally receiving a portion of the housing side wall and holding the cover member in place. The cover member 32 may include a device for disinfecting the boss 19 to prevent the spread and growth of microorganisms on the boss 19 between use. The disinfecting device includes a flange 130 depending downwardly from the cover member 32, which flange holds an absorbent material 150 (e.g., a sponge-like synthetic material) which can be impregnated with a liquid disinfectant. The absorbent material 150 is shaped and positioned so that when the cover member 32 is placed on the dispensing package 11, it surrounds and contacts the boss 19, thereby allowing the disinfectant in the absorbent material 150 to contact the boss 19.

The driving piston 301 in the first embodiment includes a series of inwardly facing stop surfaces 401–405 which extend inwardly at a series of different elevations. The housing side wall portion 16 includes a outwardly facing stop surface 400 which interacts with one of the stop surfaces 401–405 to stop further upward movement of the driving piston 301. Which stop surface 401 - 405 with which the stop surface 400 interacts is dependent upon the rotational orientation of the driving piston 301. The stop surface 400 extends for only a certain circumferential extent on the housing side wall portion 16; the remaining circumferential extent of the housing side wall portion 16 allows free movement of the driving piston 301 into the interior of the package housing 14.

In order to accurately align the driving piston 301 with the proper stop surface 401–405 so as to interact with the stop surface 400, the driving piston contains a series of alignment grooves 501 oriented above the stop surfaces 401–405. A detent 600 with a radially inwardly facing tab which interacts with the grooves 501 acts to lock the driving piston 301 into a particular rotational orientation. The radially inwardly facing tab on the detent 600 slides in the grooves 501 when the driving piston 301 is actuated. In order to change the rotational alignment of the driving piston 301, the detent 600, which is resiliently biased, is pulled radially outwardly so that the tab 601 and groove 501 are disengaged, and the driving piston 301 is rotated until the tab 601 snaps into the desired groove 501. The manner in which this is accomplished is described in U.S. patent application Ser. No. 08/099,386.

The cap 32 may include an indicia mechanism for indicating to the user the size, time and date of the last dose dispensed. A hub 303 is contained on the cap 32, the hub 303 mounting a series of indicia rings 701–703. Ring 703 can have a series of colored dots to indicate the size of dose last dispensed, which dots can be aligned with a fixed indicia on the hub 303. Rings 702 and 701 can respectively contain rings displaying time and date of last dose, with the indicia being alignable with a fixed indicia on the hub 303. Rings 701–703 and hub 303 can have interlocking detents between them to allow the indicia to be snapped into a particular alignment and prevent unwanted rotation. The manner in which such indicia are used is described in U.S. patent application Ser. No. 08/099,386. The indicia rings 701–703 could alternatively be mounted on a hub 303 on the driving piston 301, as disclosed in U.S. patent application Ser. No. 08/099,386.

In operation of the first embodiment of the present invention, a user first removes the driving piston 301 from the package 11. A container 12, generally of the conventional type for holding medications for intravenous use, is inserted into the cavity 18 so that the dip tube D is inserted into the container 12 by piercing the seal 12a. The container 12 is inserted inwardly until the upper portion of the container 12 fits snugly against the seal 22. The driving piston 301 is then inserted into the open end 15.

The user then selects the method and dose of dispensing desired. The user removes the cover member 32. If the user desires to dispense medication nasally, the replaceable dispensing passage 201 is screwed into the boss 19. If the user desires intravenous injection, the needle 202 is screwed into the boss 19 via retaining element 203. Next, the user selects the dose, by pulling out on the detent 600 and rotating the driving piston 301 until the proper stop surface 401–405 is aligned with the stop surface 400. This operation made be aided by, e.g., colored indicia or the like on the driving piston 301 which align with an arrow or the like indicia on the package 11. The detent 600 is then released, and it snaps into an aligning groove 501.

For nasal dispensing, the boss 19 is inserted into a nostril; for intravenous dispensing, the needle 202 is inserted into a vein. The user then places, e.g., the index and middle fingers F on the shoulders 901 and the thumb T on the driving piston 301. By pushing up with the thumb T (i.e., in the direction M shown in FIG. 5), the container 12 moves upwardly, pushing the pump P upwardly relative to the pump stem 13. Accordingly, liquid is dispensed either from the boss 19 as nasal spray, or through the needle 202 in a liquid form. When the appropriate stop surface 401–405 contacts stop surface 400, the container 12 is restrained from further upward movement, and dispensing stops. A metered dose of liquid from the pump P is therefore dispensed. Thumb T pressure is then released from the driving piston 301 and the spring force in the pump P pushes the pump P away from the pump stem 13. This movement causes the pump P to be refilled via the dip tube D from the container 12.

FIG. 5 shows a second embodiment of the present invention. In this embodiment of the invention, the container 12 includes a dip tube D mounted therein, and the pump P includes a tailpiece P₁ which is configured to pierce a sealing element 12a in the upper portion of container 12. After tailpiece P₁ has pierced seal 12a, it fits snugly into the interior of dip tube D, so that liquid may be drawn up through dip tube D, through tailpiece P₁ and into pump body P. The dip tube D and seal 12a may be mounted to the top of container 12 by a suitable mounting cup 12b. In all other respects, however, the structure and operation of the embodiment of FIG. 5 is identical to that of the embodiment of FIGS. 1–4.

I claim:

1. A device for dispensing metered quantities of liquid material comprising:
   a container holding a quantity of material to be dispensed;
   a housing, said container being mounted for reciprocal movement in said housing, said housing including a liquid passage, said housing comprising a pump mounted on said housing for dispensing material from an interior of said container, said container being separable from said housing and said pump, said pump including a pump stem for delivering liquid from said pump to an exterior of said container, said pump stem engaging said liquid passage; and
   a pump stroke limiting device mounted in said housing, said pump stroke limiting device limiting an amount of reciprocal movement of said container in said housing to thereby control a length of stroke of said pump.

2. The device of claim 1, further comprising:
   a driving piston connected to said container and mounted for reciprocal movement in said housing, whereby force applied to said driving piston reciprocates said container in said housing.

3. The device of claim 1, wherein:
   said housing further comprises a replaceable needle communicating with said pump stem.

4. The device of claim 1, wherein:
   said alignment tab is resiliently biased.

5. The device of claim 1, wherein:
   said container and said housing are constructed of a transparent material.

6. The device of claim 1, wherein:
   said pump comprises an element for piercing a seal on said container to provide fluid communication between an interior of the container and the pump.

7. The device of claim 6, wherein:
   said element for piercing a seal comprises a dip tube mounted on the pump, the dip tube extending into the interior of the container to provide communication between the interior of the container and the pump.

8. The device of claim 1, wherein:
   said housing further comprises a spray nozzle, said spray nozzle comprising a replaceable passage communicating with said pump stem.

9. The device of claim 8, wherein:
   said spray nozzle further comprises at least one air passage on an axially outward surface.

10. The device of claim 8 further comprising:
    a cover, said cover being attachable to said housing to thereby cover said spray nozzle.

11. The device of claim 10, wherein:
    said cover comprises a disinfecting device for providing disinfectant to the spray nozzle when said cover is attached to said housing.

12. The device of claim 10, wherein:
    said cover comprises indicia for indicating the time, date, and quantity of the last dispensed dose.

13. The device of claim 12, wherein:
    said cover comprises a hub and said indicia comprises a plurality of rotatable rings mounted on said hub.

14. A device for dispensing material from a container containing a liquid comprising:
    a housing for mounting said container for reciprocal movement therein, said housing comprising a liquid passage, said housing further comprising a pump mounted on said housing for dispensing material from an interior of said container, said container being separable from said housing and said pump, said pump comprising:
    (a) a pump stem for delivering liquid from said pump to an exterior of said container, said pump stem engaging said liquid passage, said pump stem being mounted to remain stationary relative to said housing;
    (b) a pump body mounted for reciprocal movement in said housing; and
    (c) an inlet passage for delivering liquid from said container to said pump; and
    a pump stroke limiting device mounted in said housing, said pump stroke limiting device limiting an amount of reciprocal movement of said pump body in said housing to thereby control a length of stroke of said pump.

15. The device of claim 14, wherein:
said housing further comprises a replaceable needle communicating with said pump stem.

16. The device of claim 14, wherein:
said housing comprises at least one axially outwardly facing flange to provide a surface for the application of a force opposite to a force applied to said container to permit reciprocation of said pump in said housing.

17. The device of claim 14, wherein:
said housing is constructed of a transparent material.

18. The device of claim 14, wherein:
said inlet passage comprises an element for piercing a seal on said container to provide fluid communication between an interior of the container and the pump.

19. The device of claim 18, wherein:
said inlet passage comprises a dip tube mounted on the pump, the lower end of the dip tube comprising the element for piercing the seal.

20. The device of claim 14, further comprising:
a driving piston mounted for reciprocal movement in said housing.

21. The device of claim 20, wherein:
said driving piston comprises indicia for indicating the time, date, and quantity of the last dispensed dose.

22. The device of claim 21, wherein:
said driving piston comprises a hub and said indicia comprises a plurality of rotatable rings mounted on said hub.

23. The device of claim 14, wherein:
said housing further comprises a spray nozzle, said spray nozzle comprising a replaceable passage communicating with said pump stem.

24. The device of claim 23, wherein:
said spray nozzle further comprises at least one air passage on an axially outward surface.

25. The device of claim 23 further comprising:
a cover, said cover being attachable to said housing to thereby cover said spray nozzle.

26. The device of claim 25, wherein:
said cover comprises a disinfecting device for providing disinfectant to the spray nozzle when said cover is attached to said housing.

27. The device of claim 25, wherein:
said cover comprises indicia for indicating the time, date, and quantity of the last dispensed dose.

28. The device of claim 22, wherein:
said cover comprises a hub and said indicia comprises a plurality of rotatable rings mounted on said hub.

29. A device for dispensing metered quantities of liquid material comprising:
a container holding a quantity of material to be dispensed;
a housing, said container being mounted for reciprocal movement in said housing, said housing including a liquid passage;
a pump for dispensing material from an interior of said container, said pump including a pump stem for delivering liquid from said pump to an exterior of said container, said pump stem engaging said liquid passage;
a driving piston connected to said container and mounted for reciprocal movement in said housing, whereby force applied to said driving piston reciprocates said container in said housing; and
a pump stroke limiting device mounted in said housing, said pump stroke limiting device limiting an amount of reciprocal movement of said container in said housing to thereby control a length of stroke of said pump, said pump stroke limiting device comprising a series of stop surfaces on said driving piston and a housing stop surface on said housing, one of said series of stop surfaces interacting with said housing stop surface according to a rotational orientation of said driving piston to thereby limit an amount of reciprocal movement of said container in said housing.

30. The device of claim 29, wherein:
said driving piston comprises alignment grooves corresponding with said series of stop surfaces, and wherein said housing comprises an alignment tab, said alignment tab interacting with said alignment grooves to thereby align one of said series of stop surfaces with said housing stop surface.

31. The device of claim 30, wherein:
said alignment tab is resiliently biased.

32. The device of claim 29, wherein:
said driving piston comprises indicia for indicating the time, date, and quantity of the last dispensed dose.

33. The device of claim 32, wherein:
said driving piston comprises a hub and said indicia comprises a plurality of rotatable rings mounted on said hub.

34. A device for dispensing metered quantities of liquid material comprising:
a container holding a quantity of material to be dispensed, said container comprising a dip tube;
a housing, said container being mounted for reciprocal movement in said housing, said housing including a liquid passage, said housing comprising a pump mounted on said housing for dispensing material from an interior of said container, said pump comprising a pump stem for delivering liquid from said pump to an exterior of said container, said pump stem engaging said liquid passage, said pump comprising an element for piercing a seal on said container to provide fluid communication between an interior of said container and said pump, said element for piercing a seal comprising a tailpiece mounted on said pump, wherein said tailpiece fits into an interior of said dip tube after said element has pierced said seal; and
a pump stroke limiting device mounted in said housing, said pump stroke limiting device limiting an amount of reciprocal movement of said container in said housing to thereby control a length of stroke of said pump.

35. A device for dispensing material from a container containing a liquid comprising:
(a) a housing for mounting said container for reciprocal movement therein, said housing comprising a liquid passage;
(b) a pump for dispensing material from an interior of said container, said pump comprising:
(i) a pump stem for delivering liquid from said pump to an exterior of said container, said pump stem engaging said liquid passage, said pump stem being mounted to remain stationary relative to said housing;
(ii) a pump body mounted for reciprocal movement in said housing; and (iii) an inlet passage for delivering liquid from said container to said pump;

(c) a pump stroke limiting device mounted in said housing, said pump stroke limiting device limiting an amount of reciprocal movement of said pump body in said housing to thereby control a length of stroke of said pump, said pump stroke limiting device comprising a series of stop surfaces on said driving piston and a housing stop surface on said housing, one of said series of stop surfaces interacting with said housing stop surface according to a rotational orientation of said driving piston to thereby limit an amount of reciprocal movement of said container in said housing; and (d) a driving piston mounted for reciprocal movement in said housing.

36. The device of claim 35, wherein:

said driving piston comprises alignment grooves corresponding with said series of stop surfaces, and wherein said housing comprises an alignment tab, said alignment tab interacting with said alignment grooves to thereby align one of said series of stop surfaces with said housing stop surface.

37. The device of claims 36, wherein:

said alignment tab is resiliently biased.

38. A device for dispensing material from a container containing a liquid comprising:

(a) a housing for mounting said container for reciprocal movement therein, said housing comprising a liquid passage, said housing further comprising a pump mounted on said housing for dispensing material from an interior of said container, said pump comprising:

(i) a pump stem for delivering liquid from said pump to an exterior of said container, said pump stem engaging said liquid passage, said pump stem being mounted to remain stationary relative to said housing;

(ii) a pump body mounted for reciprocal movement in said housing; and (iii) an inlet passage for delivering liquid from said container to said pump, said inlet passage comprising an element for piercing a seal on said container to provide fluid communication between an interior of said container and said pump, said inlet passage further comprising a tailpiece mounted on said pump, said lower end of said tailpiece comprising said element for piercing said seal; and (b) a pump stroke limiting device mounted in said housing, said pump stroke limiting device limiting an amount of reciprocal movement of said pump body in said housing to thereby control a length of stroke of said pump.

* * * * *

UNITED STATES PATENT AND TRADEMARK OFFICE
CERTIFICATE OF CORRECTION

PATENT NO. : 5,433,343

DATED : 18 July 1995

INVENTOR(S) : Philip MESHBERG

Page 1 of 2

It is certified that error appears in the above-identified patent and that said Letters Patent is hereby corrected as shown below:

| Column | Line | |
|--------|------|---|
| 1 | 30 | Change "---" to -- -- --. |
| 2 | 10 | Change "here in" to --herein--. |
| 3 | 45 | After "that" insert --it--. |
| 3 | 50 | Change "he" to --the--. |
| 4 | 27 | Change "such a" to --such as--. |
| 4 | 49 | Change "a end" to --an end--. |
| 4 | 60 | Change "the" to --a--. |
| 6 | 15 | After "includes" change "a" to --an--. |
| 7 | 13 | Change "made" to --may--. |

UNITED STATES PATENT AND TRADEMARK OFFICE
CERTIFICATE OF CORRECTION

PATENT NO. : 5,433,343
DATED : 18 July 1995
INVENTOR(S) : Philip MESHBERG It is certified that error appears in the above-identified patent and that said Letters Patent is hereby corrected as shown below:

| Column | Line | |
|---|---|---|
| 8 | 12 | Delete "said alignment tab is resiliently biased." and insert --said housing comprises at least one axially outwardly facing flange to provide a surface for the application of a force opposite to a force applied to said container to permit reciprocation of said container in said housing.-- |
| 9 | 50 | Change "claim 22" to --claim 27--. |

Signed and Sealed this

Nineteenth Day of November, 1996

Attest:

BRUCE LEHMAN

*Attesting Officer*    *Commissioner of Patents and Trademarks*